(12) United States Patent
Blanc et al.

(10) Patent No.: US 6,371,903 B1
(45) Date of Patent: Apr. 16, 2002

(54) THERAPY PROBE

(75) Inventors: Emmanuel Blanc, St. Genis Laval (FR); Christian Chaussy, Strasslach; Stefan Thüroff, Munich, both of (DE)

(73) Assignee: Technomed Medical Systems, S.A. (FR)

( * ) Notice: Subject to any disclaimer, the term of this patent is extended or adjusted under 35 U.S.C. 154(b) by 98 days.

(21) Appl. No.: 09/599,666

(22) Filed: Jun. 22, 2000

(51) Int. Cl.[7] ................................................ A61H 1/00
(52) U.S. Cl. ............................ 600/2; 600/439; 600/459
(58) Field of Search ............................... 600/459, 439, 600/462; 601/2, 3, 4; 604/22

(56) References Cited

U.S. PATENT DOCUMENTS

| | | | |
|---|---|---|---|
| 4,858,613 A | 8/1989 | Fry et al. | 128/660.03 |
| 4,955,365 A | 9/1990 | Fry et al. | 128/24 A |
| 5,020,539 A | 6/1991 | Yokoi et al. | 128/662.06 |
| 5,036,855 A | 8/1991 | Fry et al. | 128/660.03 |
| 5,316,000 A | 5/1994 | Chapelon et al. | 128/660.03 |
| 5,474,071 A | 12/1995 | Chapelon et al. | 128/660.03 |
| 5,676,692 A | 10/1997 | Sanghvi et al. | 607/97 |
| 5,720,287 A | 2/1998 | Chapelon et al. | 128/660.03 |
| 5,762,066 A | 6/1998 | Law et al. | 128/660.03 |
| 6,071,238 A | 6/2000 | Chapelon et al. | 660/439 |

OTHER PUBLICATIONS

N. Bom et al., "Early and recent intraluminal ultrasound devices", International Journal of Cardiac Imaging, 4:79–88 (1989).

*Primary Examiner*—Brian L. Casler
*Assistant Examiner*—Runa Shah Qaderi
(74) *Attorney, Agent, or Firm*—Welsh & Katz, Ltd.; Eric D. Cohen

(57) ABSTRACT

An ultrasound therapy probe includes a therapy transducer movably mounted on a probe body, a partially deformable flexible casing disposed around the therapy transducer, and a guard ring that limits deformations of the flexible casing when the transducer moves with respect to the probe body. The therapy transducer can be moved between a therapy position and a retracted position, and the guard ring provides an end-of-travel stop against which the therapy transducer bears when in a therapy position. A first opening is provided for injecting liquid into the flexible casing, and a second opening is provided for withdrawing liquid from the flexible casing. The second opening is located on the guard ring so that bubbles are withdrawn from the flexible casing as soon as they form.

14 Claims, 4 Drawing Sheets

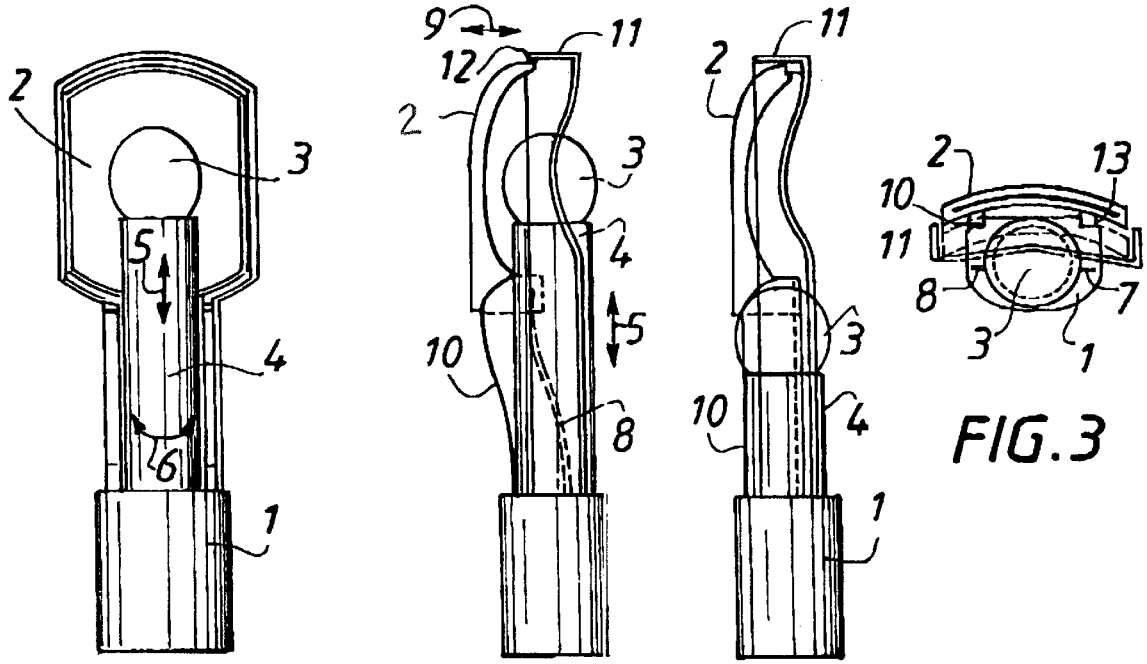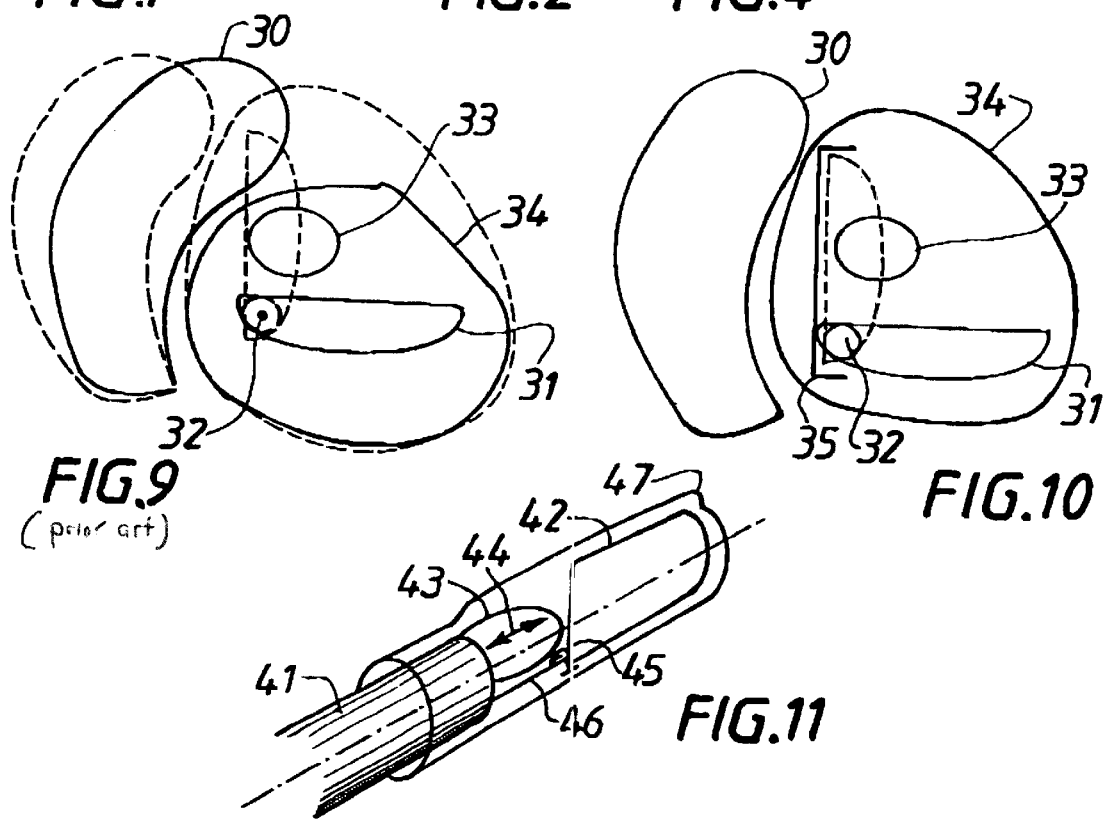

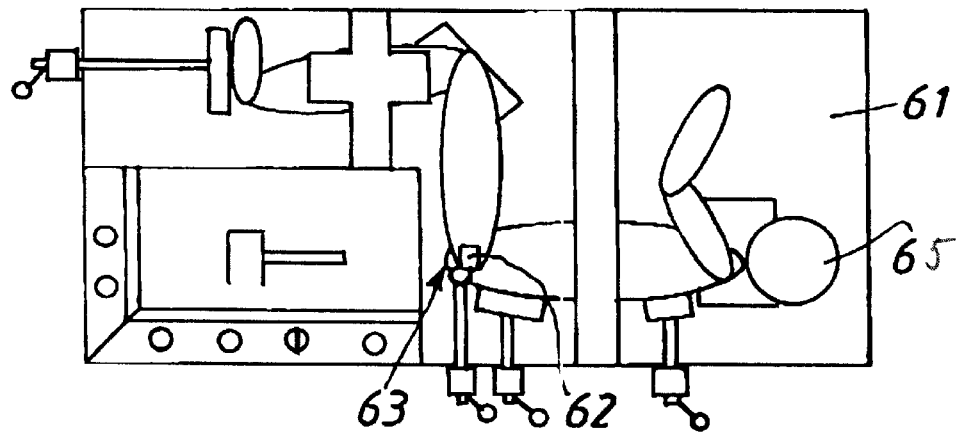
FIG.16
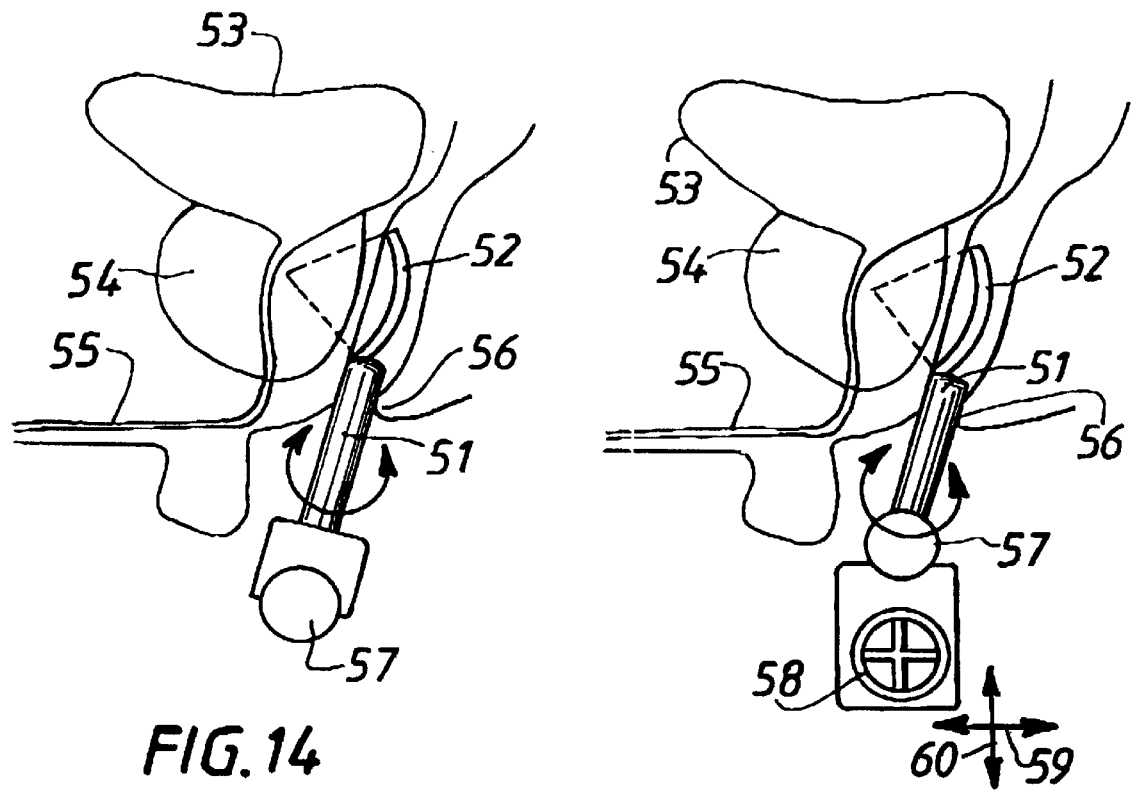
FIG.14
FIG.15

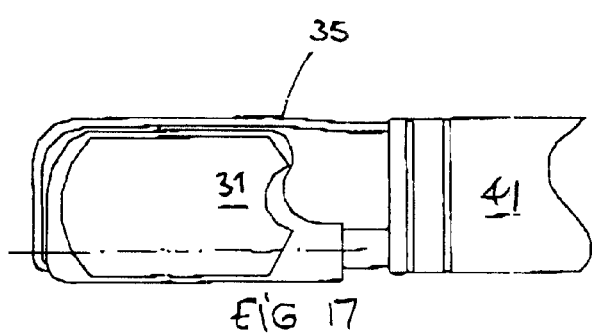
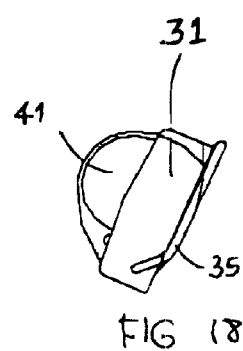
FIG 17
FIG 18
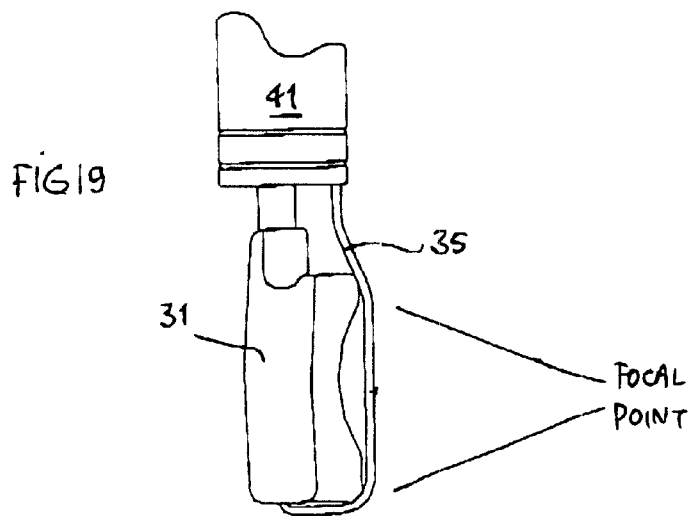
FIG 19
FOCAL POINT
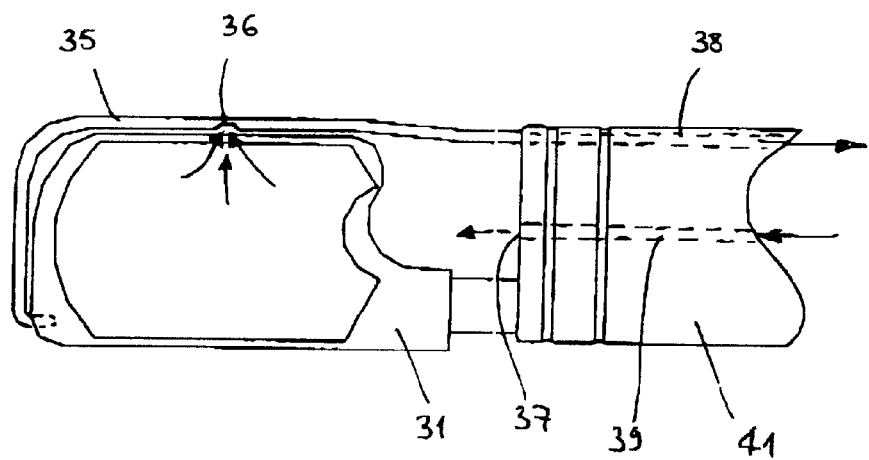
FIG 20

THERAPY PROBE

BACKGROUND OF THE INVENTION

The present invention relates to a therapy probe, which includes a therapy transducer movably mounted on a probe body. Such probes are used for prostate treatment using focused ultrasound, via rectal application. Such probes are also used for treating the esophagus, the stomach, the liver and, more generally in percutaneous treatment or treatment by laparoscopy.

The probes advantageously include an imaging transducer that enables the treated region to be visualized during treatment.

WO-A-8907909 discloses a therapy and imaging probe for endocavital use, including a therapy transducer that is movable in a rotary manner, and an imaging transducer that is movable linearly. The linear and rotational movements are independent.

FR-A-2,673,542 (WO-A-9215523 or U.S. Pat. No. 5,474,071) discloses a therapy and imaging probe, including a spoon-shaped therapy transducer with an associated imaging transducer. The two transducers do not move with respect to each other.

FR-A-2,708,207 discloses a therapy and imaging probe, including a spoon-shaped therapy transducer. The therapy transducer is movable in a rotary manner, and the imaging transducer is movable linearly. FR-A-2,715,822 discloses a therapy and imaging probe in which the therapy transducer and the imaging transducer are movable and are driven by common drive means. U.S. Pat. No. 5,720,287 claims priority of these two French applications.

N. Bom et al., "Early and recent intraluminal ultrasound devices", International Journal of Cardiac Imaging, 4:79–88 (1989), discloses various types of imaging or treatment probes.

U.S. Pat. No. 5,762,066 discloses a therapy probe having a rotatable transducer and non-distentable acoustic membrane to ensure that tissue does not protrude into an interior volume of the probe housing. This reference suggests circulating a degassed coupling fluid to cool the probe and prevent the formation of bubbles.

The above-described therapy probes seek to provide therapy that is as effective and accurate as possible. If an imaging transducer is provided, another goal is to allow the treated region to be visualized, preferably during treatment. Finally, regarding endocavital probes, the total probe volume or cross-section is also an important parameter.

With respect to prior art probes, it has been suggested to insert the probe into a flexible casing or to provide a flexible casing in the probe. After the probe is inserted into the body cavity, the flexible casing may be deformed into contact with the tissue of the patient. The casing is deformed, e. g. by inflating it with a liquid. Such liquid may include degassed water. For example, see FR-A-2,715,822 or U.S. Pat. No. 5,676,692. U.S. Pat. No. 5,720,287 also discloses a probe with a flexible casing. The flexible casing is inflated during treatment, and fluid is circulated to cool the transducers.

EP-A-0 815 901 discusses the problem of patient movement during treatment. Such movement can lead to the probe moving with respect to the patient, or moving with respect to the organ to be treated or visualized. The reference also discusses the guiding and maintaining of the probe with respect to the patient. In international application WO-A-8907909 for prostate treatment, it is proposed to apply a rotary movement about the general axis of a rectal probe. In FR-A-2,673,542 for prostate treatment, an endorectal treatment and imaging probe is provided, together with a urethral imaging probe. While the two probes are being positioned, it is proposed to move the probes in the plane of symmetry of the patient to bring the probes closer together or further apart. The relative position of the probes is then "frozen" for treatment. During treatment, the two probes are rotated independently of each other about their respective longitudinal axes, and are moved linearly along their parallel longitudinal axes, i.e. essentially parallel to the rectum. FR-A-2,708,207 proposes a probe mounted for linear movement in three directions, and for rotation about its longitudinal axis. FR-A-2,715,822 discloses a probe mounted for rotation about its longitudinal axis in a collar fixed to one end of a rod. The other end of the rod is mounted in a swivel joint allowing rotation in a vertical plane. The swivel joint is mounted for linear movement along two axes, in the same vertical plane.

Yet another problem discussed in EP-A-0 815 901 involves movements of the probe with respect to the organ to be treated. As discussed above, rotation of the probe about its longitudinal axis creates problems as it can lead to movement of the organ to be treated, particularly if the probe does not have a cylindrical cross-section. This particular problem does not occur in the case of the probe disclosed in FR-A-2,715,822 where the therapy transducer and the imaging transducer are arranged inside a rigid, cylindrical probe body. This solution, however, increases probe diameter or requires a decrease in the size of the therapy transducer, which is difficult to achieve. To overcome these problems, EP-A-0 815 901 suggests using a guard ring for limiting deformation of the flexible casing at the time a therapy transducer moves from a therapy position to an imaging position.

SUMMARY OF THE INVENTION

The invention resolves problems associated with prior art probes. Some of the above-described problems apply to all probes regardless of whether they include an imaging transducer, while other problems occur when the probes have both a therapy transducer and a imaging transducer.

Some of the problems addressed by the prevent invention relates to inflation of the flexible casing. The casing is deflated for inserting the probe into the cavity so as to facilitate insertion of the probe, typically in the case of a rectal or urethral probe. The casing is then inflated to ensure contact with the tissues of the patient. A liquid is used to inflate the casing and to permit transmission of the ultrasound from the transducers through the liquid. One problem discovered by the inventors of the present invention is that inflation of the casing causes bubbles to appear in the liquid. If the fluid is circulated during treatment, e.g. for the purposes of cooling the transducers, the bubbles may cause problems before they eventually disappear. Another problem is that bubbles may appear during treatment due to the ultrasound waves. Such bubbles have not been eliminated in prior art devices.

The present invention provides a solution to the problem of bubble formation in the liquid when liquid is used to inflate the flexible casing. The above-described problems are resolved by the present invention, which provides a therapy probe for use in a body cavity including a therapy transducer mounted on a support and movable with respect to a probe body between a therapy position and a retracted position. Also included is an at least partially deformable flexible casing around the therapy transducer, a guard ring for limiting deformations of the flexible casing in front of the transducer when the transducer is moved with respect to the probe body from the therapy position to the retracted position, a first opening for injecting liquid into the flexible casing, and a second opening for withdrawing liquid from the flexible casing, where one of the openings is formed on the guard ring.

The present invention also provides a therapy apparatus including the probe described above and a pump connected to the probe for circulating liquid in the flexible casing through the first and second openings.

In a preferred embodiment of the invention, the therapy transducer is rotatable about an axis substantially parallel to the longitudinal axis of the probe, and the guard ring extends from the probe body to a point on the transducer located on the axis. It is advantageous that the therapy transducer have a rectangle shape and that the guard ring extend along two adjacent sides of the transducer. The opening formed on the guard ring may be located substantially in the middle of the length of the guard ring. In another embodiment of the invention, the guard ring is formed of a tube, such as a metallic tube.

Other features and advantages of the present invention will become more apparent from the description that follows of various embodiments, provided by way of example, and with reference to the attached drawings.

BRIEF DESCRIPTION OF THE DRAWINGS

FIG. 1 is a front view of a probe according to a first embodiment of the invention shown in the imaging position;

FIG. 2 is a side view of the probe in FIG. 1, shown in the imaging position;

FIG. 3 is a sectional top view of the probe in FIG. 1, shown in the imaging position;

FIG. 4 is a side view of the probe in FIG. 1, shown in the firing position;

FIG. 9 is a diagrammatic sectional view of a prior art probe shown in both the firing position and in the imaging position;

FIG. 10 is a diagrammatic sectional view of a probe according to a third embodiment of the invention shown in both the firing position and in the imaging position;

FIG. 11 is a diagrammatic view of a forth embodiment of the invention;

FIGS. 14 and 15 are diagrammatic sectional views of probes according to the invention, shown in position for prostate treatment by rectal application;

FIG. 16 is a diagrammatic view showing a patient in the position for treatment with a probe, according to the invention;

FIG. 17 is a front view of the transducer of a probe, together with its guard ring;

FIG. 18 is a side view of the probe of FIG. 17;

FIG. 19 is a side view of the probe of FIG. 17; and

FIG. 20 is a view of the probe of FIG. 17, showing circulation of fluid.

DETAILED DESCRIPTION OF THE INVENTION

Figure 5:
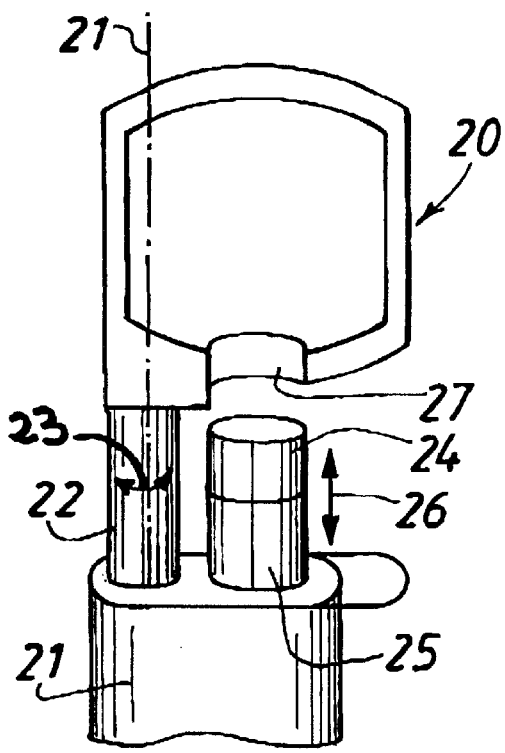
FIG. 5 is a front view of a therapy transducer according to a second embodiment of the invention.

In the drawings, therapy probes are shown which include a therapy transducer 2 and an imaging transducer 3. This invention also applies when the probe includes only the therapy transducer 2, as explained with reference to FIGS. 9 to 11. Thus, application of this invention does not require both types of probes to be included.

FIG. 1 is a front view of a probe according to a first embodiment of the invention shown in the imaging position illustrating the forward end of the probe. FIG. 1 also shows the extremity of a probe body 1, the therapy transducer 2 and the imaging transducer 3.

The therapy transducer 2 is movable with respect to probe body 1, between a therapy or firing position (see FIG. 4) and a retracted position (see FIG. 2), which permits, operation of the imaging transducer 3. An arrow 9 indicates movement of the therapy transducer 2 between the firing position and the retracted position. The therapy transducer 2 is mounted on the probe body on thin plates 7 and 8, which are flexible in a plane perpendicular to the plane of FIG. 1. Thus, the therapy transducer 2 is able to move linearly substantially perpendicular to the plane of the figure, i.e., substantially perpendicular to the longitudinal axis of the probe, or right to left as shown in FIGS. 2 and 4. The therapy transducer 2 is mounted in the probe body 1 via four thin flexible plates 7, 8, 10, and 13 situated at both sides of imaging probe support 4. The thin plates 7 and 8 are positioned ahead of the imaging probe support, while the thin plates 10 and 13 are positioned toward the rear of the imaging plate support, as shown in FIGS. 2 and 3.

Imaging transducer 3 is mounted on a support 4 configured to move linearly with respect to the probe body 1 between a retracted position (FIG. 4) and an imaging position (FIGS. 1–2), as indicated by an arrow 5. In a specific embodiment, the imaging transducer 3 is also rotatably mounted so as to be rotatable about an axis parallel to the longitudinal axis of the probe, thus permitting the imaging transducer to perform a sweep in a transverse plane perpendicular to the longitudinal axis of the probe, as indicated by an arrow 6. This ensures full sweeping of the region to be treated. Rotation of the imaging transducer 3 can be obtained by rotation of the probe support 4.

In the embodiment of FIG. 1, the therapy transducer 2 is a spoon-shaped therapy transducer of the type disclosed in FR-A-2,673,542 to which reference can be made for further details. Imaging transducers of the types disclosed in FR-A-2,673,542 or FR-A-2,708,207 can also be used.

FIG. 2 is a side view of the probe in FIG. 1 shown in the imaging position. In FIG. 2, elements described with reference to FIG. 1 can be recognized, as well as the third thin plate 10 supporting the therapy transducer 2. As shown in FIG. 2 in the imaging position, the imaging transducer 3 via its support 4 pushes the therapy transducer 2 back to retain it in its retracted position.

FIG. 2 also shows a guard ring 11 that acts as a stop against which the therapy transducer 2 bears when in the treatment position. The nature and function of the guard ring 11 will become more apparent from the description of FIGS. 9 and 10. Maintaining means, such as magnets 12, enable the therapy transducer 2 to be maintained in the firing position. The maintaining means 12 may also be used to detect the presence of the therapy transducer 2 in the firing position.

FIG. 3 is a top sectional view of the probe in FIG. 1 shown in the imaging position. In FIG. 3 the dotted lines indicate the firing position of the therapy transducer 2 bearing against the guard ring 11. FIG. 3 shows the four thin plates 7, 8, 10 and 13 supporting the therapy transducer 2.

FIG. 4 is a side view of the probe in FIG. 1 shown in the firing position. In the firing position, the imaging transducer 3 is in the retracted position, while the therapy transducer 2, under the action of the thin flexible plates, is brought into the firing position such that it bears against the guard ring 11.

The probe in FIGS. 1–4 operates as follows: for endocavital use, the imaging transducer 3 is brought to the retracted position by moving probe support 4 linearly towards the probe body 1. The therapy transducer 2 under the action of the thin flexible plates is then brought towards guard ring 11 into the therapy position, as shown in FIG. 4. In this position, the probe has a minimal cross-section allowing ready introduction into a body cavity such as, for example, the rectum of a patient.

Once the probe has been positioned substantially opposite the organ to be treated, the imaging transducer 3 is advanced from the retracted position (FIG. 4) towards the imaging position (FIG. 3). The movement of the imaging transducer 3 (upwards toward the guard ring 11) causes movement of the therapy transducer 2 (right to left as shown in FIGS. 2 and 4) from its firing position (FIG. 4) to its retracted position (FIG. 2). In the embodiment of FIG. 1, the imaging transducer 3 slides along the inner surface of the therapy transducer 2 and exerts a force on the therapy transducer, which is opposed by the thin flexible plates 7, 8, 10 and 13, thus forming a recall or spring means.

The organ to be treated can then be visualized using the imaging transducer 3 by turning the probe support 4 of the imaging transducer 3, as needed. Such visualization allows accurate positioning of the probe.

To proceed with treatment, the imaging transducer 3 is brought back to the retracted position without moving the probe, and the therapy transducer 2 again adopts, under the action of the recall means, its firing position (FIG. 4). Treatment can then proceed while providing simultaneous visualization, as explained with reference to FIG. 8. The presence of the guard ring 11 ensures that the wall of the organ to be treated remains immobile during movement of the transducers inside the probe, as explained with reference to FIGS. 10 to 12. One can then switch between the imaging position and the firing position, depending on the desired treatment protocol.

Various means known to one of ordinary skill in the art may be used for controlling or detecting imaging transducer 3 movement, such as stepping motors, rack and pinion gears, endless screws, jacking means, etc. Similar means may be used for detecting the position of the therapy transducer 2. Further detail on this subject can be obtained by referring to French applications FR-A-2,673,542, FR-A-2,708,207 or FR-A-2,715,822.

There has been no mention in the description with reference to FIGS. 1 to 4 of the means for controlling or driving the imaging transducer 3 and therapy 2 transducer. Nor has there been a description of the outer flexible casing enclosing the complete transducer and guard ring assembly, which bears some similarity to that in FR-A-2,673,542 and FR-A-2,708,207.

Compared to the probes in the reference documents, the probe in FIGS. 1 to 4 combines a small cross-section, which probe is easily introduced into a body cavity, with a simplicity of control of the relative movements of the transducers 2 and 3. Indeed, according to the present invention, it is not necessary to provide independent drive means for the imaging transducer 3 and the therapy transducer 2. This greatly simplifies the structure of the probe and reduces its overall volume. The guard ring 11 ensures that the probe is maintained in the proper position with respect to the organ to be treated. Physical displacement of the therapy transducer 2 is reduced compared to known devices, while permitting treatment in a more restricted volume or body cavity. This is accomplished without causing movement of the organ to be treated when changing from the firing position to the retracted position, or vice-versa.

In the embodiment of FIGS. 1 to 4, the therapy transducer 2 is mounted on the recall means consisting of the thin flexible plates 7, 8, 10, and 13. Other recall means, such as small rods associated with springs, can also be employed. Provision can also be made for the recall of the therapy transducer 2 from its retracted position to its firing position by means for driving the imaging transducer 3 after the imaging transducer has reached its retracted position.

In the probe of FIGS. 1–4, means are provided for inflating the casing with a liquid. There are provided first and second openings in the vicinity of the end of the probe. When the flexible casing is affixed to the probe, the first and second opening are located inside of the flexible casing. The openings are used for injecting liquid into the casing and for withdrawing liquid from the casing. One of the openings is located on the guard ring. This provides the advantages discussed below in reference to FIGS. 17–20.

FIG. 5 is a front view of a probe according to a second embodiment of the invention. The therapy transducer 20 is movably mounted with respect to a probe body 21 for rotation with respect to a shaft 22, as indicated symbolically by an arrow 23. An imaging transducer 24 is mounted on a support 25 and is able to move linearly with respect to the probe body 21, as shown symbolically by arrow 26.

Toward a lower portion of probe body 21, and opposite the imaging transducer 24, the therapy transducer 20 has a recess 27, which is formed, for example, by milling or other suitable manufacturing process to facilitate unimpeded passage of the imaging transducer.

Figure 6:
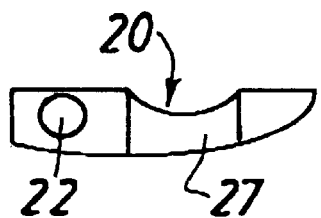
FIG. 6 is a bottom view of the transducer of FIG. 5.

FIG. 6 is a bottom view of the therapy transducer 20 of FIG. 5. In FIG. 6, the shaft 22 and the recess 27 are shown. The therapy transducer 20 has the shape of a self-focusing "spoon," as described in FR-A-2,673,542.

In another embodiment, the shaft 22 is rotatably controlled with respect to the probe body 21 by drive means, such as that disclosed in French application FR-A-2,673,542. However, in a preferred embodiment, the therapy transducer 20 is not movable independently of the imaging transducer 24, and is simply urged by the recall means. For example, the shaft 22 may be rotatably mounted in the probe body 21 for movement over a limited angular range, and is urged by a torsion spring toward one of the extreme positions of the angular range, which may correspond to the firing position.

Figure 7:
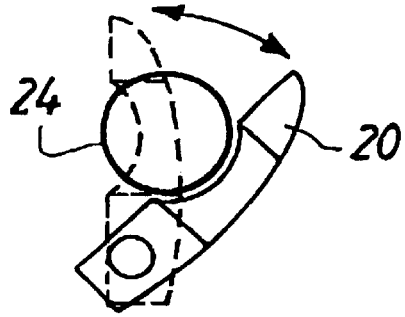
FIG. 7 is a bottom sectional view of the therapy transducer of FIGS. 5–6 and the corresponding imaging transducer.

FIG. 7 is a partial sectional bottom view of the therapy transducer 20 and imaging transducer 24 of FIGS. 5 and 6, shown in the imaging position. In FIG. 7, the therapy transducer 20 is shown in solid lines in its retracted position, while the dotted lines illustrate the firing position. The imaging transducer 24 is shown in solid lines in its imaging position. The retracted position, however, is not shown because it is not in the plane of the cross-section.

Figure 8:
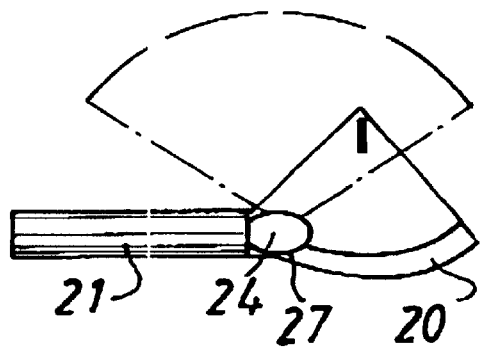
FIG. 8 is a partial sectional side view of the probe shown in the firing position.

FIG. 8 is a partial sectional side view of the probe according to a second embodiment of the invention showing the therapy transducer 24 in the firing position. When the therapy transducer 20 is in the firing position, the imaging transducer 24 is situated inside the recess 27 on the lower portion of the therapy transducer. As in the embodiment of FIGS. 1–4, openings are provided for inflating the casing and/or introducing circulating liquid, and where at least one of the openings is preferably located on the guard ring 11.

Operation of the probe according to the second embodiment may be similar to operation of the probe as disclosed in FR-A-2,708,207. Some operational aspects, however, are different, as set forth below. First, it is not necessary to provide drive means for the therapy transducer 20. The therapy transducer 20 moves from its firing position to its retracted position due to the action of the imaging transducer 24 when the imaging transducer moves from its retracted position to its imaging position. Specifically, when the imaging transducer 24 moves from its retracted position to the imaging position, it urges the therapy transducer 20 back to the retracted or non-firing position, where such retraction is opposed by the recall means. When the imaging transducer 24 is moved to the retracted position or non-imaging position, the recall means urges the therapy transducer 20 back to the firing position. Thus, the advantages of simplicity of structure and operation are obtained, as described above with reference to the first embodiment.

Second, the presence of the recess 27 enables the imaging transducer 24 in its retracted position to be close to the therapy transducer 20, as shown in FIG. 8. Thus, with respect to the probe disclosed in FR-A-2,708,207, the present invention allows superior observation of the organ to be treated using the imaging transducer 24, even during treatment. This "zone of superior observation" is shown in FIG. 8 by arc-like regions exposed by the therapy transducer 20 and by the imaging transducer 24, respectively. Furthermore, the recess 27 limits the maximum angular movement of the therapy transducer 20 to permit treatment to be performed in a more restrictive volume, which avoids movement of the organ to be treated. Finally, in the case of prostate treatment, if the imaging transducer 24 in its retracted position is too far from the therapy transducer 20, as can be the case with the probe disclosed in FR-A-2,708, 207, the imaging transducer 24 is aligned at the level of the anus, which is barely transparent to ultrasound. This is avoided in the present invention due to the recess 27.

Obviously, two features of the invention described above, namely the recall means for the therapy transducer 20 and the recess 27, may be independently implemented. One can also provide the recess 27 in the embodiment shown in FIGS. 1–4, or eliminate the recess in the embodiment shown in FIGS. 5–8.

FIG. 9 is a diagrammatic sectional view of a prior art probe, showing both the firing position and the imaging position. The sectional view is shown in a plane substantially perpendicular to the longitudinal axis of the probe, and shows an organ 30 to be treated. FIG. 9 shows the prior art probe according to FR-A-2,708,207 in solid lines in the imaging position, while the dotted lines represent the firing position. The organ to be treated 30, may be, for example the prostate, which may be treated via the rectum. The probe includes a therapy transducer 31, which is rotatable about a shaft 32, an imaging transducer 33, and a flexible casing or balloon 34 enveloping the probe. As explained in the above-referenced documents, the balloon 34 is inflated with a liquid, such as degassed water, in order to make contact with the wall of the organ to be treated to ensure passage of the ultrasound from the therapy transducer 31, through the liquid, and into the organ to be treated. When the probe is in the imaging position, the practitioner locates the prostate, draws or designates the contours of the region to be treated, and then changes to the firing position. In the firing position, the imaging transducer 33 is retracted into the probe body, and the therapy transducer 31 is rotated 90° around the shaft 32 so as to position the therapy transducer 31 opposite the organ to be treated, as shown in dotted lines in FIG. 9. Due to the movement of the therapy transducer 31, however, it is possible that the organ to be treated will not exactly occupy the same position in both the firing and imaging positions, as is the case with prior art probes. This is because movement of the therapy transducer 31 may cause movement of the balloon 34, which, in turn, may cause movement of the organ to be treated 30. This leads to location errors and the danger of inadvertently treating healthy regions, or of failing to treat unhealthy regions. In the case of prostate treatment, the additional danger of burning the rectal wall exists. The present invention proposes a solution to this problem.

It is clear that the above-described problem not only exists when the probe includes movable therapy and imaging transducers, but also exists when the probe includes only a movable therapy transducer. For example, this may be true where there is provision for sweeping the target, even if the probe does not include an imaging transducer.

FIG. 10 is a cross-sectional diagrammatic view of a probe according to a third embodiment of the invention, shown in both the firing position and in the imaging position. This view corresponds to the view shown in FIG. 9, and illustrates the solution provided by the present invention to the new problem disclosed above with reference to FIG. 9. Reference numerals that are identical to those in FIG. 9 represent identical or corresponding elements.

According to the present invention, the probe has a guard ring 35 that maintains the organ to be treated 30 and the balloon or envelope 34 in the same position regardless of whether the therapy transducer 31 and imaging transducer 33 are moved between the imaging position and the therapy position. Specifically, the guard ring 35 limits deformations of the flexible casing or envelope 34 when the therapy transducer 31 moves.

The guard ring 34 is advantageously shaped so as to have a contour close to that of the therapy transducer 31. This ensures that the probe has a minimal cross-section when in its firing position, and further ensures easy introduction of the probe into a body cavity. This feature also permits use of a therapy transducer having a relatively large surface area, like in the transducer disclosed in FR-A-2,708,207, but without needing to increase the size of the probe.

The guard ring 35 can have the shape of a ring surrounding the therapy transducer 31, as shown in FIG. 10. The guard ring 35 may be made of any suitable material, for example, a pressed metal plate having an outer profile close to that of the therapy transducer 31, as shown in FIGS. 1–4. The guard ring 35 may also have the shape of a disc, having, at least at its center, an acoustically-transparent window allowing therapy or imaging waves to pass through. The guard ring 35, for example, may be made of metal, or any other sufficiently rigid material that ensures that the organ to be treated is appropriately held or contacted. In this case, it is possible for the flexible casing or balloon 34 to only extend to the back of the guard ring 35, where the guard ring itself would constitute the wall of the probe in contact with the organ to be treated. Such a configuration would even further reduce any possible movement of the organ to be treated when the flexible casing is deflated. In such a case, the flexible casing 34 is only partially deformable on the same side of the guard ring as the transducer. One can also provide for the flexible casing 34 to be fixed to the guard ring 35. As discussed above, the probe is provided with openings for circulating a liquid through the casing, and at least one of the openings may be located on the guard ring. The ring may be in the form of a hollow tube, or it may also be provided with additional tubing, e.g. where it is made of a pressed metal plate.

As discussed below, it is advantageous that the opening used for withdrawing the liquid be located on the guard ring 35 near the therapy transducer 31 when the therapy transducer is in the firing or therapy position. For this embodiment, as well as for the other embodiments, more than one opening may be provided on the guard ring 35. For example, there may be openings for withdrawing liquid located on both sides of the therapy transducer 31. One could create a flow of liquid in front of the therapy transducer 31 by injecting liquid from one side of the guard ring 35 and withdrawing the liquid from the other side of the guard ring.

FIG. 11 is a diagrammatic view of the fourth embodiment of the present invention showing a probe body 41, a therapy transducer 42 and an imaging transducer 43, where an arrow 44 shows linear movement of the imaging transducer along a longitudinal axis of the probe. An arrow 45 shows the rotational movement of the therapy transducer 42 about a shaft 46.

In the embodiment of FIG. 11, a guard ring 47 has the general shape of a ring, the contour of which is substantially that of therapy transducer 42. The guard ring 47 is mounted on the probe support means, and the probe body 41 can freely rotate with respect to the guard ring. This solution has the advantage of ensuring perfect immobility of the organ to be treated with respect to the guard ring 47, even if the probe body 41 rotates about its longitudinal axis to provide a lateral sweep during therapy. The openings for the liquid are not shown on FIG. 11 for reasons of clarity.

Figure 12:
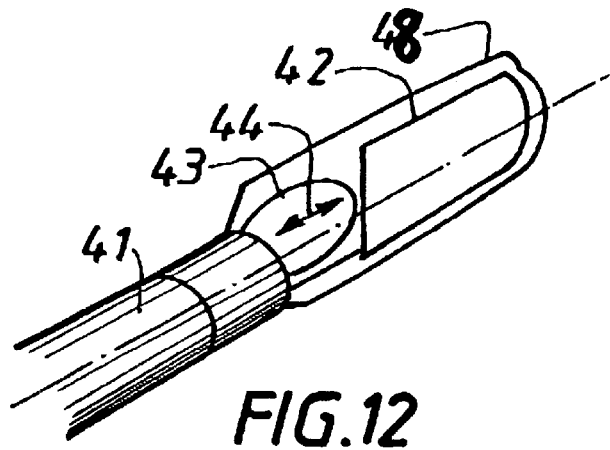
FIG. 12 is a diagrammatic view of a fifth embodiment of the invention.
Figure 13:
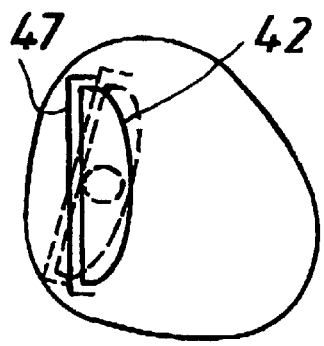
FIG. 13 is a diagrammatic sectional view of the probe shown in FIGS. 9–10.

FIG. 12 is a diagrammatic view of a fifth embodiment of the invention. This embodiment is substantially identical to the embodiment of FIG. 11, except that a guard ring 48 is mounted on the forward end of the probe body 41. This embodiment is advantageous because of the simplicity of implementation, and because a minimal cross-section of the probe is achieved. However, it is possible in this case that the organ to be treated may move slightly if the probe body 41 is rotated about its longitudinal axis to provide a lateral sweep during therapy, as shown on FIG. 13 in solid lines and dotted lines. This movement, however, is of very limited amplitude when compared to the movements that are likely to occur in the prior art probes described with reference to FIG. 9. Again, the openings for injecting and withdrawing liquid are not shown in FIGS. 12 and 13.

Clearly, the present invention can be implemented with other embodiments of the invention, alone or in combination. Thus, a guard ring may be provided in the first embodiment of the invention, as shown on FIGS. 1 to 4, or it may be omitted in view of the limited movements of the therapy transducer in this embodiment. In the second embodiment of the present invention, a guard ring may also be provided, even if angular displacement of the therapy transducer is limited.

The presence of a guard ring is particularly advantageous when, as explained with reference to FIGS. 1 to 8, the therapy transducer is mounted on recall means and moves from its therapy position to its retracted position under the action of the imaging transducer when the imaging transducer is moved from its retracted position to its imaging position. When the imaging transducer is retracted, the guard ring acts as an "end-of-travel" stop for the therapy transducer, thereby ensuring accurate positioning. One can also provide means for maintaining the therapy transducer on the guard ring, which makes it possible to maintain the therapy transducer against the guard ring. Alternatively, one may provide detection means to sense the position of the therapy transducer against the guard ring to enable firing.

With respect to the above-described embodiments, the presence of a guard ring is advantageous to ensure that the organ to be treated is maintained in proper position during movement of the transducers. Further, the guard ring limits the deformations of the partially deformable casing or envelope that surrounds the movable therapy transducer. This ensures that the organ to be treated is maintained in its proper position, and further permits construction of a probe having a minimal cross-section.

FIGS. 14 and 15 show two cross-sectional diagrammatic views of probes according to the invention, in a position for treating the prostate by rectal application when the patient is normally positioned in the "gun-dog" lying position on a treatment table. Shown are a probe 51 having a therapy transducer 52, a bladder 53, a prostate 54, a urethra 55 and a rectum 56 of the patient.

According to the invention, the probe 51 is mounted on a ball joint 57 to allow easier introduction into the rectum. Because of the ball joint 57, the probe 51 can be positioned so that its longitudinal axis is precisely parallel to the patient's rectum. This avoids wounding the patient and facilitates easy introduction of the probe. As shown in FIG. 15, the ball joint 57 is advantageously mounted on displacement means 58 making it possible to move the probe linearly along three axes. Two of the axes are shown symbolically by arrows 59 and 60 of FIG. 15, while the third axis is perpendicular to the plane of the figure. In other words, the third axis is perpendicular to the plane of the treatment table.

The present invention thus provides vertical movement of the probe 51, i.e., movement in a direction transverse to the longitudinal axis of the probe and transverse to the main direction of propagation of the therapy waves.

Movement in a direction perpendicular to the axis of the figures permits treatment of larger volumes, while limiting rotation of the probe. With respect to treatment of the prostate, such movement makes it possible to provide accurate adjustment of the probe position for treating lobes of the prostrate without having to significantly rotate the probe about its longitudinal axis. Movement may or may not be provided by a motor. If a motor is employed, motor-driven movement that is transverse to the direction of propagation of therapy waves may be used to ensure a sweep of the organ to be treated, while avoiding or limiting rotation of the probe body about its axis. Even if a motor is not used, such movement nevertheless makes it possible, in the case of large organs, to perform manual adjustment in the treatment medium thereby limiting the amplitude of rotation of the probe.

The present invention thus makes it possible to preserve throughout the course of treatment a treatment field in the direction of propagation that is always substantially perpendicular to the surface of the organ to be treated. In the plane of FIGS. 14 and 15, i.e. in the plane of the main direction of propagation of the therapy waves, movement of the probe may be motor-driven. Alternatively, the motor may be omitted. In one embodiment of the invention, movement by a motor is provided, but the probe is also configured to be moved manually. This has several advantages. First, during introduction of the probe, the practitioner can readily check the probe's position and measure resistance to introduction. This avoids wounding the patient through motor-driven movement of the probe because the power of the motor may not be well controlled and perceived by the practitioner. Second, manual movement of the probe makes it possible to define a reference point so as to limit movements of the probe provided by the motor. Thus, the initial position of the probe, as determined manually, corresponds to the mean position. Movement of the probe via the motor with respect to this mean position can be limited to a maximum predetermined distance.

In another embodiment of the invention, movement of the probe during treatment is provided using different displacements in the various directions. Indeed, a volume can be treated by juxtaposing individual lesions, i.e. individual "shots," by moving the transducer along two sweep directions of the volume to be treated. These two directions are directions generally perpendicular to the direction of propagation of the beam, and correspond to a mode of treatment in which the volume is treated in successive planes that are substantially perpendicular to the direction of propagation of the waves.

This mode of treatment involves the following new problem: it is possible that the therapy transducer may generate an asymmetrical beam, typically if the probe is rectangular shape or has a shape similar to that shown in FIG. 1. In this case, due to the lack of symmetry of the ultrasound beam, use of a constant pitch to juxtapose the lesions in the two directions will lead either to lesions being superimposed over each other in one direction, or to an intermediate untreated region in the other direction.

The ultrasound beam is not necessarily symmetrical, depending on the shape of the transducer. In the case of a therapy transducer having a rectangular shape, the lesions produced at the focus are consequently elliptical in cross-section, with the smallest diameter corresponding to the largest width of the transducer.

To resolve this new problem, particularly for transducers having an elongated focal spot, such as with rectangular transducers, the present invention proposes to adapt the firing pitch of the therapy transducer to shape of the lesion. For example, a rectangular transducer having dimensions 50 mm×35 mm, the optimum firing pitch is 1.6 mm in the longitudinal direction, and 2.3 mm in the lateral direction. The present invention thus proposes that the means for moving the probe provide such movement with a different pitch in the various directions.

FIG. 16 is a diagrammatic plan view of a patient shown in position for treatment with a probe. FIG. 16 shows a patient 65, on a treatment table 61, supported if necessary by cushions. The patient 65 is prevented from moving by straps or adjustable spacers. Notwithstanding, it is still possible that the patient will move slightly during the course of treatment. There is then a danger of the probe shifting with respect to the patient, leading to incomplete or inappropriate treatment.

To warn the practitioner of this situation and to allow him to check the suitability of treatment, the patient is provided with a light barrier making it possible to detect patient movement. For example, a reflector 62 may be attached to the patient's hip, and a transmitter/receiver 63 may be provided on the treatment table 61 or on a point that is fixed with respect to the table. Any suitable reflector or transmitter/receiver known to one skilled in the art may be used. The light barrier shown in FIG. 16 is arranged in a plane perpendicular to the plane of the treatment table for detecting movements of the patient in the direction of the treatment table. Such movements are most frequently encountered.

The invention makes it possible to ensure that the patient's 65 position is maintained and that the organ to be treated, in this case, the prostate, is fixed in space. This makes it possible to employ a probe mounted on a drive unit that is fixed with respect to the treatment table. One can thereby accurately control movements of the probe with respect to the organ to be treated.

The present invention not only applies to treatment, but also applies to periods of time before and after treatment, separate from the actual treatment phase, and may also apply to imaging. In this regard, the term "treatment table" does not imply that the patient is necessarily undergoing treatment when the invention is applied. The invention is, thus, not limited to a method for therapeutic treatment of the human body. Pre-treatment and post-treatment regimens are also applicable.

In another embodiment, the probe of the invention includes means for circulating the liquid used for inflating the flexible casing surrounding the therapy transducer. The circulation means, for example, may include at least two channels within the probe body that permit coupling liquid to fill the flexible casing and to circulate within. The probe is then connected to a circulation pump and to a liquid reservoir or other suitable means.

Compared to prior art solutions having a single inflation channel in a flexible casing, the present invention makes it possible, due to circulation of the liquid, to evacuate bubbles that eventually form during treatment and/or to allow cooling of the transducer(s) and/or the wall of the organ to be treated. Indeed, bubbles can form in the liquid due to heating of the liquid or due to cavitation affects resulting from the ultrasonic waves emitted by the transducer. Circulation of the liquid makes it possible to limit bubble formation, thereby improving the effectiveness of treatment and limiting probe heating.

Advantageously, the liquid is provided with thermostatic control. Circulating the thermostatically-controlled liquid constitutes a simple and effective way of cooling the therapy transducer or the imaging transducer. Fluid circulation also makes it possible to cool, or maintain at a low temperature, that part of the organ to be treated in contact with the probe. This limits or eliminates surface burns of the patient, and in the case of prostate treatment, limits or eliminates burning of the rectal wall.

FIG. 17, is a front view of the transducer of a probe with the guard ring 35. This probe is similar to the probe shown in FIGS. 9–11, in that the therapy transducer is rotatable with respect to an axis parallel to the axis of the probe. FIG. 17 shows the front part of the probe 41, the guard ring 35, and the therapy transducer 31. The flexible casing is not shown in FIG. 17. Note that the shape of the guard ring 35 has substantially the same contour as the outside contour of the transducer. This maximizes the size of the transducer, while minimizing the overall transverse dimension of the probe. Accordingly, insertion of the probe into a body cavity, such as the rectum, is made easier.

The transducer of FIG. 17 has a substantially rectangle shape, as seen in a plane transverse to the emission of ultrasound, and is rotatable about a longitudinal axis of the transducer. The guard ring 35 extends substantially along two sides of the transducer, that is, along the length of the transducer opposed to the axis, and along the width of the transducer opposed to the probe body.

FIG. 18 is a side view of the probe of FIG. 17, and shows that the end of the guard ring 35 extends into a hole of the transducer. The hole is located on the axis of rotation of the transducer. Thus, the guard ring 35 extends only on two sides of the transducer, while limiting movement of the flexible casing in front of the transducer. FIG. 19 is a side view of the probe of FIG. 17, where the arrow shows the location of the second opening for withdrawing the coupling liquid from the flexible casing.

FIG. 20 is a side view of the probe of FIG. 17, showing circulation of fluid. A first opening 37 is included for injecting fluid into the flexible casing (not shown), and a second opening 36 is included for withdrawing fluid from the inside of the flexible casing. As discussed above, channels or ducts 38 and 39 are provided in the probe body for connection to a liquid reservoir and to a liquid pump. According to the invention, one of the openings is formed in the guard ring 35. The guard ring 35 is preferably made of a rigid tube, such as a stainless steel tube. The tube may have an outer diameter of 3 mm and an inner diameter of 2 mm. The metallic tube does not interfere with emission of ultrasound because the guard ring 35 lies around the therapy transducer when the transducer is in the therapy position.

The opening located on the guard ring 35 is preferably the second opening 36, used for withdrawing fluid. The first opening may be located at the end of the probe body. The inventors have realized that positioning the second opening 36 on the guard ring 35 was more effective for eliminating bubbles from the coupling liquid. Indeed, when the casing is inflated, bubbles trapped near the end of the probe are pushed away by the liquid being injected through the first opening 37. During operation of the transducer, bubbles that formed near the transducer surface are immediately withdrawn from the flexible casing. Last, in the operating position of the patient 65 shown in FIG. 16, the probe body is substantially horizontal, and the guard ring is substantially vertical. The second opening is then higher than the first opening and is located in the upper part of the flexible casing. This again facilitates withdrawing of bubbles from the flexible casing.

In FIG. 20, the second opening 36 is located on the tube, preferably in the middle of the length of the guard ring 35, while the first opening 37 is connected to channel 39. Liquid thus circulates from channel 39 through the first opening 37, and into the flexible casing. Liquid is withdrawn through the second opening 36 into the tube forming the guard ring. It then flows back to the pump and/or reservoir through the channel 38. Circulation of liquid is represented by arrows on FIG. 20. As discussed above, the number of openings could vary, as well as their location on the guard ring.

The preferred embodiments of the invention may be subject to variations: the various features of the various embodiments described can be combined or used alone, depending on requirements. Application of the probe to prostate treatment is only one example of possible treatments. The probe of the present invention can also be used for the treatments mentioned above.

What is claimed is:

1. A therapy probe for use in a body cavity comprising:
a therapy transducer mounted on a support, the therapy transducer movable with respect to a probe body between a therapy position and a retracted position;
a partially deformable flexible casing disposed around the therapy transducer;
a guard ring configured to limit deformations of the flexible casing when the therapy transducer is moved with respect to the probe body between the therapy position and the retracted position;
a first opening for injecting liquid into the flexible casing;
a second opening for withdrawing liquid from the flexible casing; and
where at least one of the openings is formed in the guard ring.

2. The probe recited in claim 1 wherein the therapy transducer is rotatable about an axis substantially parallel to the longitudinal axis of the probe, and wherein the guard ring extends from the probe body to a point of said transducer located on said axis.

3. The probe recited in claim 2 wherein the therapy transducer has a rectangle shape, and wherein the guard ring extends on two adjacent sides of the transducer.

4. The probe recited in claim 3 wherein the opening formed in the guard ring is located substantially in the middle of a length of the guard ring.

5. The probe recited in claim 1 wherein the guard ring is formed as a tube.

6. The probe recited in claim 5 wherein the tube is metallic.

7. The probe recited in claim 1 wherein the second opening is formed on the guard ring.

8. A therapy apparatus, comprising:
a probe for use in a body cavity including:
a therapy transducer mounted on a support and movable with respect to a probe body between a therapy position and a retracted position;
an at least partially deformable casing around the therapy transducer;
a guard ring to limit deformations of the casing in front of the transducer when the transducer is moved between the therapy position and the retracted position;
a first opening for injecting liquid into the flexible casing;
a second opening to permit withdrawal of liquid from the flexible casing, wherein one of the openings is formed in the guard ring; and
a pump connected to the probe for circulating liquid in the casing through the first and second openings.

9. The apparatus recited in claim 8 wherein the therapy transducer is movable in rotation about an axis substantially parallel to the longitudinal axis of the probe, and wherein the guard ring extends from the probe body to a point of transducer located on said axis.

10. The apparatus recited in claim 9 wherein the therapy transducer has a rectangle shape, and wherein the guard ring extends on two adjacent sides of said transducer.

11. The apparatus recited in claim 10 wherein the opening formed in the guard ring is located substantially in the middle of a length of said guard ring.

12. The apparatus recited in claim 8 wherein the guard ring is tubular in shape.

13. The apparatus recited in claim 12 wherein the guard ring is formed of metal.

14. The probe recited in claim 1 wherein the second opening is formed on the guard ring.

* * * * *

UNITED STATES PATENT AND TRADEMARK OFFICE
CERTIFICATE OF CORRECTION

PATENT NO. : 6,371,903 B1
DATED : April 16, 2002
INVENTOR(S) : Blanc et al.

It is certified that error appears in the above-identified patent and that said Letters Patent is hereby corrected as shown below:

<u>Column 14,</u>
Line 16, presently recites "ring extends from the probe body to a point of said transducer located on said axis." this should be corrected to read -- ring extends from the probe body to a point on said transducer located on said axis. --
Line 52, presently recites "guard ring extends from the probe body to a point of transducer located on said axis." this should be corrected to read -- guard ring extends from the probe body to a point on said transducer located on said axis. --

Signed and Sealed this

Twelfth Day of November, 2002

*Attest:*

*Attesting Officer*

JAMES E. ROGAN
*Director of the United States Patent and Trademark Office*